United States Patent [19]
Eckstein et al.

[11] 4,083,226
[45] Apr. 11, 1978

[54] PORTABLE EXPLOSION-PROOF GAS DETECTOR

[75] Inventors: Wolfgang Eckstein, Sereetz; Horst Rabenecker, Klein Parin, both of Germany

[73] Assignee: Drägerwerk Aktiengesellschaft, Germany

[21] Appl. No.: 755,654

[22] Filed: Dec. 30, 1976

[30] Foreign Application Priority Data

Jan. 28, 1976 Germany .............. 2603064

[51] Int. Cl.² ............................................. G01N 1/22
[52] U.S. Cl. .................................. 73/23; 73/421.5 R
[58] Field of Search ............... 73/23, 23.1, 421.5 R; 200/19 M; 417/477; 23/232 R, 232 E, 254 R, 254 E

[56] References Cited
U.S. PATENT DOCUMENTS

| 1,960,790 | 5/1934 | Muffly .................. 200/19 M |
| 3,137,240 | 6/1964 | Hunt .................... 417/477 |
| 3,138,104 | 6/1964 | Cantor .................. 417/477 |
| 3,233,060 | 2/1966 | Wintriss ............... 200/19 M |
| 3,391,570 | 7/1968 | Becker et al. ............ 73/23 |
| 3,410,059 | 11/1968 | Garnier .............. 73/421.5 R |
| 3,429,176 | 2/1969 | Topham ................. 73/23.1 |
| 3,956,940 | 5/1976 | Guild ............... 73/421.5 R |

Primary Examiner—Richard C. Queisser
Assistant Examiner—Stephen A. Kreitman
Attorney, Agent, or Firm—McGlew and Tuttle

[57] ABSTRACT

A portable explosion-proof gas detection device, comprises a housing which defines an interior flameproof motor chamber with an electric motor in the chamber having a pump drive shaft which extends outwardly into a pump chamber having a rotor connected to the electric motor shaft. The rotor engages a hose connection which is arranged in an openable chamber and which is engaged by a rotor over a pump squeezing surface defined the housing surrounding wall. The hose is connected through a twin fitting to a holder for a testing tube which has an opening at each end is positionable in a tube holder so that its open end is oriented in an opening in the housing for the inflow of air through the tube and through the pump for discharge out of the housing. The apparatus includes a control knob which actuates an electrical control circuit which is magnetically actuable by rotation of the knob to energize the electric motor from a battery source which is also arranged within the housing. The housing includes a cover which includes an end and a top wall portion which, when lifted upwardly, provides an access to the contact tube holder and also to the pump tube fitting to permit the replacement thereof, if necessary.

7 Claims, 4 Drawing Figures

PORTABLE EXPLOSION-PROOF GAS DETECTOR

FIELD AND BACKGROUND OF THE INVENTION

This invention relates in general to the construction of gas detection devices and, in particular, to a new and useful portable explosion-proof gas detector construction.

DESCRIPTION OF THE PRIOR ART

The present invention relates to an electrically operated portable explosion-proof gas detection device in which gaseous substances are directed through indicator tubes for the purpose of checking their gas consituency. In spaces or in an atmosphere with dangerous gas-vapour or gas-air mixtures, electrical apparatus are used which must be designed in accordance with particular regulations. Those parts of the apparatus which might ignite the explosive mixture have to be enclosed in a manner such that sparks produced in their interior cannot lead to an explosion of the mixture present in the ambience.

A portable device adapted for directing gaseous substances through indicator tubes is known, which comprises a housing in which a battery, an electric motor, a diaphragm pump driven by the motor, and a holder for the indicator tube are accommodated. The housing is of cylindrical shape. The holder for the indicator tube is mounted in one of its front walls, and in the other front wall, a plug connection is provided for recharging the battery. The safety against explosion is obtained by sealing the battery, the charging transformer, and the protective resistors with plastic.

In such a design, protection against explosion is obtained by following the regulations for intrinsic safety. In view of the intrinsic safety, the electric energy is reduced to a value preventing ignition sparks. The high-speed diaphragm pump is intrinsically safe. The suction capacity of these pumps is insufficient, however.

Because of the valves necessary for their operation, diaphragm pumps are susceptible to contamination and corrosion. With the indicator tube positioned at the pressure side, measuring errors due to the continuing presence of gases in supply lines and in the diaphragm pump are unavoidable. Another measuring error results from the dead volume in front of the indicator tube. Thus must not be neglected since the requirements on the measuring accuracy increase continuously (German Offenlegungsschrift 1,933,047).

SUMMARY OF THE INVENTION

The present invention is directed to a portable gas detector for directing gaseous mixtures through indicator tubes, of a design such that it can be operated in an ambience containing ignitable mixtures and so that it furnishes exact measuring values in measurements of both short and long duration and even of very small concentrations.

To this end, in accordance with the invention, a common housing is provided in which the electric motor and a contact tube of the switch are accommodated in a first, air-tight chamber, a suction pump is mounted in a second chamber outside the first chamber, and the control knob of the switch is mounted in a third chamber.

The invention advantageously provides that the indicator tube is disposed at the suction side of the pump so that the air sample is taken in directly from the ambient atmosphere. The sample has not yet been adulterated by residues of previous measurements. The use of a pump having a satisfactory suction capacity is made possible by accommodating the part involving the explosion hazard, i.e., the drive motor, in an air-tight chamber designed in accordance with the requirements of the protection against explosion hazards. The other parts of the detector are mounted, in a manner suitable for their operation, in further chambers which need not be explosion-proof. Due to the solution with a single air-tight chamber, the device is of small size and remains easily portable.

The suction pump is a well-known hose pump in which the hose is squeezed and released by the action of a rotor moving over a squeezing surface which is formed by the inside of a front wall which is hinged to the housing and can be swung out. Both ends of the hose loop are connected to a twin fitting which is retained in a guide recess of the front wall. Due to this simple design, the hose is easily accessible, and can be checked and exchanged without any difficulty.

According to a development of the invention, the operating switch circuit comprises a closed electrical contact tube which is mounted in the air-tight chamber and a magnetic control means for controlling said switch. The magnetic control means includes a rotary control knob which is mounted outside the air-tight chamber for actuating the contacts without engagement therewith by a permanent magnet. Due to this design, the protection against explosion is preserved and, at the same time, a simple and secure operation of the switch is insured.

To arrest the knob in the adjusted "on" or "off" position in a simple manner, the knob is provided with locking surfaces which apply against a hinged wall portion of the housing in respective end positions.

The gas detector, in accordance with the invention, operates reliably in any ambience containing ignitable mixtures and even in measurements of long duration. Since the indicator tube is positioned at the suction side, exact measuring values are obtained even with small concentrations of the gases to be measured in the gas mixture.

Accordingly, it is an object of the invention to provide a portable, explosion-proof, gas detection device, which comprises a housing which defines an interior air-tight motor and operating contact chamber which contains the electric motor and the contact switch for operating the motor and which advantageously includes magnetic control means for effecting the contact and opening of the contact switch for the motor which is located outside of the air-tight chamber and which also includes a pump which is operated from the shaft of the motor in a separate compartment and which has a connection to a holder for a testing tube having an opening which is positionable over the holder and an opposite end which is open to draw the test gases in through an opening in the housing and to discharge them out of the housing.

A further object of the invention is to provide a portable, explosion-proof, gas detection device which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference should be had to the accompanying drawings and descriptive matter in which there are illustrated preferred embodiments of the invention.

DESCRIPTION OF THE PREFERRED EMBODIMENT

Figure 1:
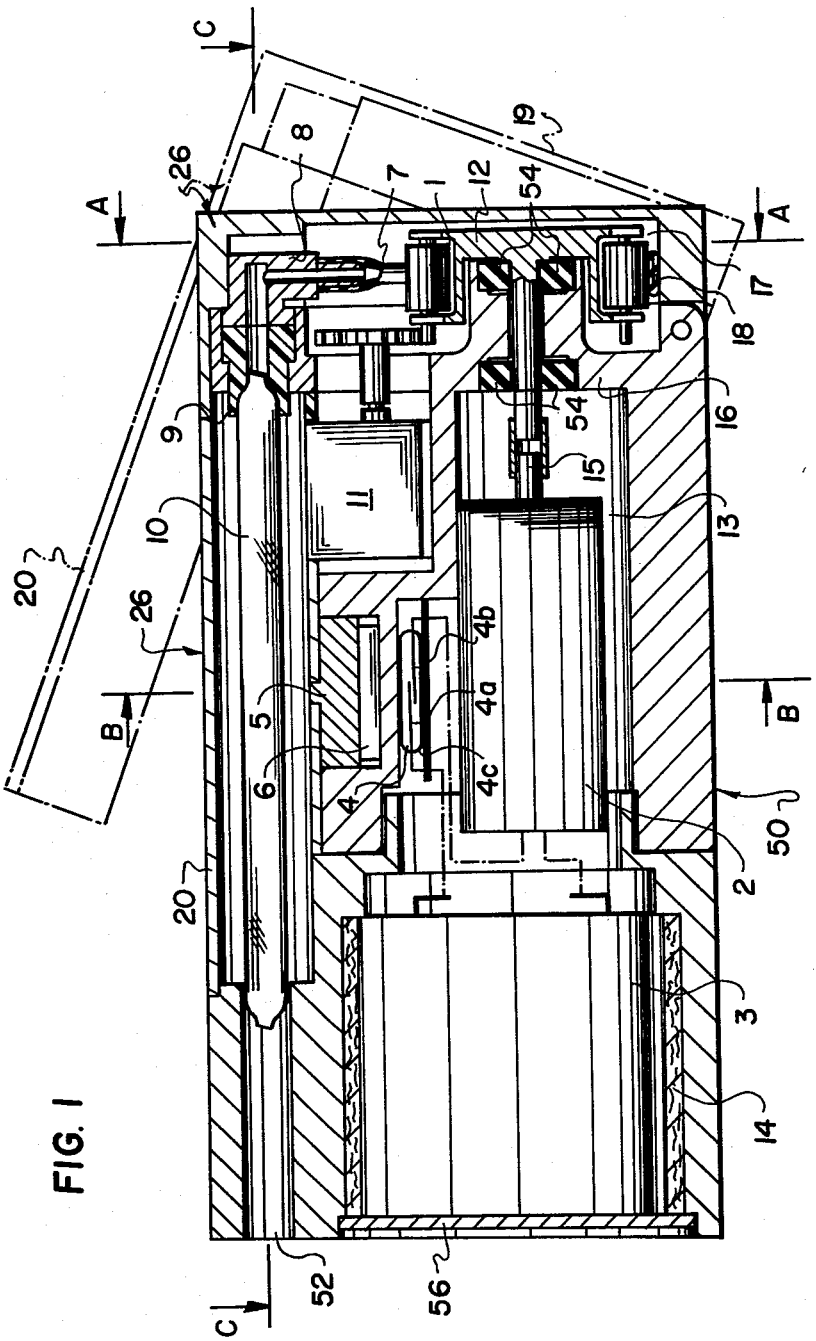
FIG. 1 is a longitudinal sectional view of a gas detection device constructed in accordance with the invention.

Referring to the drawings in particular, the invention embodied therein, comprises a portable, explosion-proof gas detector, which includes a hose pump, generally designated 1, which operates as a suction pump and is driven by an electric motor 2 which is powered by a rechargeable battery 3.

In accordance with the invention, the device includes a housing, generally designated 50, which includes an air-tight chamber 13 in which there is positioned an electric motor 2 which is operated or turned on and off by a contact control 4 which is also contained in this chamber. Contact 4 includes the two contact arm portions 4a and 4b located in a closed tube 4c. A control means for operating contacts 4a and 4b comprises a rotary control knob 5 which carries a permanent magnet 6 for actuating the switching contacts.

Figure 2:
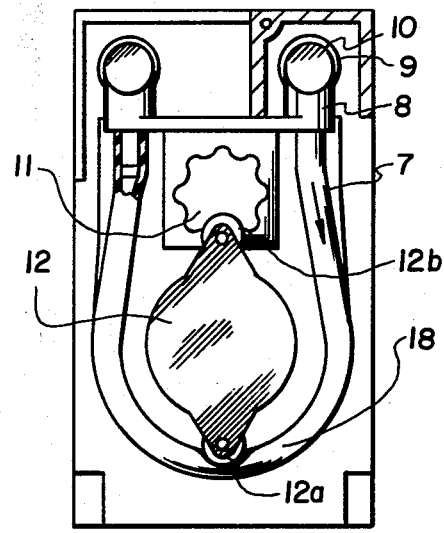
FIG. 2 is a section taken along the line A—A of FIG. 1.
Figure 3:
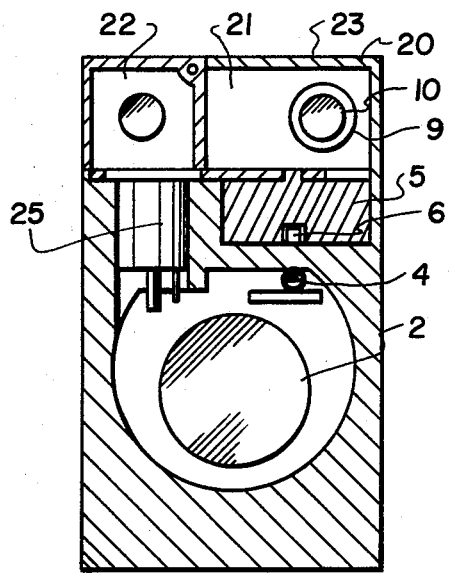
FIG. 3 is a section taken along the line B—B of FIG. 1.

In accordance with a feature of the invention, the hose pump 1 comprises a hose loop 7 with both ends connected to respective terminals of a twin fitting 8, as best seen in FIG. 2. The suction side of twin fitting 8 is connected to a tubular holder 9 having a front end with a recess opening for accommodating an open end of a testing tube or indicator tube 10. The opposite end of indicator tube 10 is also opened and positioned at the inner end of an inlet passage 52 defined in housing 50.

The pump means includes a rotor 12 which is secured to the drive shaft 15 of drive motor 2 extends flame-proof through a wall in ball-bearings 54. The rotor carries opposite rollers 12a and 12b which engage with a rotatable counterwheel 11 and with a portion of hose 7 over a squeezing surface 18 defined in an end wall portion of an openable cover 26. The counterwheel 11 counts the revolutions of rotor 12 which is a measure of the amount of air taken in through the indicator tube 10. Electric motor 2 and actuating switch 4 are mounted in an air-tight chamber 13 of the housing and this chamber is designed to meet the requirements for explosion safety regulations. A front wall of the chamber includes a battery chamber part 14 which is closed by a cover 56. The battery 3 is electrically connected to motor 2 and contact tube or control 4 by means of slip rings which are not shown.

Figure 4:
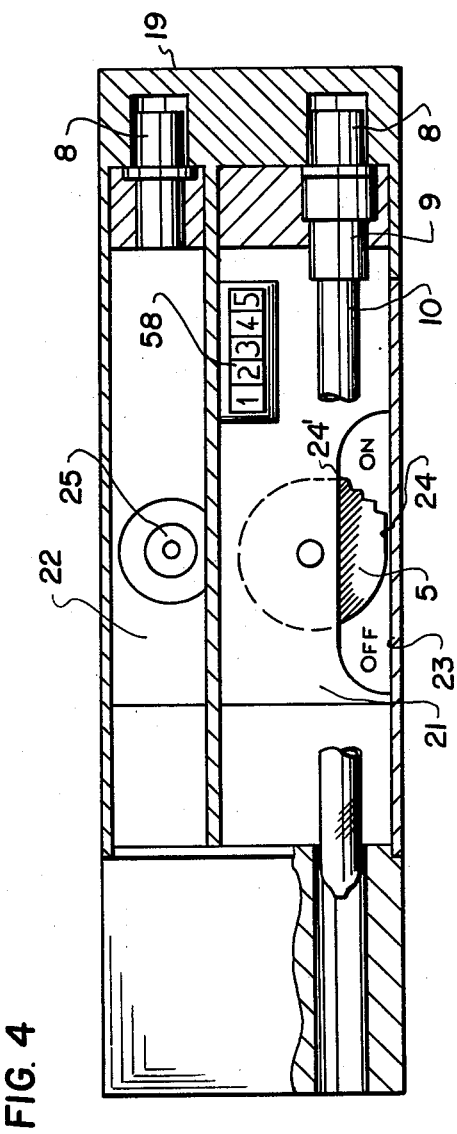
FIG. 4 is a section taken along the line C—C of FIG. 1.

The openable cover 26 includes a front wall portion 19 and a top wall portion 20 and the constructions is such that they define with the housing, two separate chambers 21 and 22. In addition, top wall 20 is provided with a hinged cover portion 23, as shown in FIG. 4, which may be opened for access to the holder 9 with the testing tube 10 and also to the display mechanism 58 of counter 11. In addition, control knob 5 for the switch is accessible in this chamber and it is provided with end surfaces 24 and 24' which provide end stops for each end position of "on" and "off." Thereby, control knob 5 will be retained in the respective switch position.

A charging connection for electrical charging purposes 25 is provided for charging battery 3. The charging connection is accessible on swinging out cover 26 which comprises the front wall 19 and the top wall 20. In the closed position, front wall 19 retains twin fitting 8 in place. After cover 26 has been swung out, twin fitting 8 and hose loop 7 can be removed and the hose may be exchanged, if desired.

The gas detector operates as follows:

Upon opening cover 23, indicator tube 10 is inserted into holder 9. By turning control knob 5 into an "on" position, permanent magnet 6 becomes effective to cause the contacts of contact tube 4 to become closed and the electric circuit between the electric motor 2 and the battery 3 is closed. By closing cover 23, control knob 5 is arrested in its position. Motor 2, and consequently, the hose pump 1 are in operation. Air is taken in through the twin fitting 8, holder 9 and indicator tube 10. The air is discharged through the pressure side of twin fitting 8 into chamber 22 and, therefrom, into the open air. When the measuring operation is terminated, control knob 5 is turned back into its "off" position, and the number of revolutions of the rotor of hose pump 1 is read on counter 58. This reading makes it possible to determine the volume of air which has been taken through the testing tube 10. This makes it possible to evaluate the indication of the tube.

To charge battery 3, cover 26 is pivoted outwardly, so that the charging device can be connected to charging connection 25. If needed, in this position of cover 26, twin fitting 8 and hose loop 7 may be removed, in order to check or exchange hose 7. Cover 26 may be secured against tampering by a special screwed connection, which has not been shown.

While a specific embodiment of the invention has been shown and described in detail to illustrate the application of the principles of the invention, it will be understood that the invention may be embodied otherwise without departing from such principles.

What is claimed is:

1. A portable, explosion-proof gas detection device, comprising a housing defining an interior air-tight motor chamber and an electrical operating contact chamber, an electrical motor in said motor chamber, said motor having a pump drive shaft extending out of said chamber, an operating electrical contact for starting and stopping said motor located in said electrical operating contact chamber, said housing also defining a pump chamber adjacent said motor chamber and said electrical operating contact chamber and also defining a testing tube receiving chamber adjacent said motor chamber and said electrical operating contact chamber, said testing tube receiving chamber having a test gas inlet opening adjacent one end and defining a test tube receiving recess adjacent its opposite end, a testing tube holder adjacent the opposite end of said testing tube receiving chamber opposite to and spaced from the recess to permit insertion of a testing tube between said holder and the recess and having a gas passage therethrough, pump means in said pump chamber having an inlet connected to said holder gas passage to draw test gas through said inlet through the testing tube and into said test holder gas passage and for discharging it out of said housing, and electrical circuit control means in said housing electrical operating contact chamber connected to said electric motor for operating said motor to drive said pump means; said housing having a removable cover portion overlying said testing tube receiving chamber.

2. A portable, explosion-proof gas detection device, according to claim 1, wherein said electrical circuit control means comprises a movable control member having a magnet for operating said operating contact.

3. A portable, explosion-proof gas detection device, according to claim 1, wherein said pump means comprises a hose, said housing defining a squeezing surface disposed around a portion of the periphery of said hose, and a rotor rotating against said hose to squeeze it against said surface to effect pumping, said housing being a cover pivotally mounted on said housing for closing and opening said pump chamber and carrying said squeezing surface.

4. A portable, explosion-proof gas detection device, according to claim 1, wherein said pump means includes a twin fitting having a pump inlet connection extending to said testing tube holder, said housing having a front wall portion enclosing said twin fitting.

5. A portable, explosion-proof gas detection device, according to claim 1, wherein said housing includes a separate chamber for accommodating said electrical circuit control means, said electrical circuit control means comprising a rotary knob having a magnet thereon movable adjacent said operating contact for starting and stopping said motor.

6. A portable, explosion-proof gas detection device, according to claim 1, wherein said electrical circuit control means comprises a rotatable knob, said housing having a chamber in which said knob is rotatable, said knob having stopping surfaces at spaced locations thereon and being rotatable in said housing between said stopping surfaces which bear against a portion of said housing.

7. A portable, explosion-proof gas detection device, comprising a housing defining an interior air-tight motor and operating contact chamber, an electrical motor in said motor and operating contact chamber, said motor having a pump drive shaft extending out of said chamber, an operating contact for starting and stopping said motor located in said chamber, said housing also defining a pump chamber adjacent said motor and operating contact chamber and a contact tube receiving chamber adjacent said motor and operating contact chamber, said testing tube receiving chamber having a test gas inlet opening adjacent one end, a testing tube holder adjacent the opposite end of said contact tube receiving chamber, pump means in said pump chamber having an inlet connected to said holder to draw test gas through said inlet through the testing tube and into said test holder and for discharging it out of said housing, and electrical circuit control means in said housing connected to said electric motor for operating said motor to drive said pump means wherein said pump chamber is defined in an end wall of said housing, said electrical motor shaft extending from said motor chamber through a wall of said housing into said pump chamber, said pump including a rotor affixed to said shaft, a twin fitting located in said pump chamber having an inlet connection to said holder and terminating in a hose fitting in said pump chamber and having a discharge connection spaced from said inlet connection, a length of hose connected between said inlet fitting and said discharge fitting of said twin fitting and engaged around said rotor, and a pivotal housing closure having a wall portion defining a squeezing surface disposed around a portion of the periphery of said hose, said rotor being rotatable to squeeze the portion of said hose to effect pumping, a counter comprising a rotatable counterwheel having recesses therein disposed in the path of said rotor and being engageable by said rotor during rotation thereof to rotate and record the number of rotations of said rotor, and a digital indication connected to said wheel and being actuatable thereby to indicate the number of revolutions of said rotor.

* * * * *